United States Patent
Pauley et al.

[19]

[11] Patent Number: 6,060,640
[45] Date of Patent: May 9, 2000

[54] MULTIPLE-LAYER, FORMED-IN-PLACE IMMUNOISOLATION MEMBRANE STRUCTURES FOR IMPLANTATION OF CELLS IN HOST TISSUE

[75] Inventors: Robin G. Pauley, Ingleside; Donna L. McLarty, Hoffman Estates; Atul R. Khare, Palatine; Shmuel Sternberg, Northbrook; Daniel R. Boggs, Libertyville; Steven Neuenfeldt, Vernon Hills; Mark Jones, Winnetka; James H. Brauker; Laura A. Martinson, both of Lake Villa, all of Ill.

[73] Assignee: Baxter International Inc., Deerfield, Ill.

[21] Appl. No.: 08/446,210

[22] Filed: May 19, 1995

[51] Int. Cl.[7] .............................. A61F 2/02; C12N 5/08; A61M 31/00; A61D 7/00

[52] U.S. Cl. ..................... 623/11; 623/1; 623/2; 623/3; 623/12; 623/13; 623/16; 623/18; 623/66

[58] Field of Search ................... 623/1, 2, 3, 10, 623/11, 12, 16, 18, 66

[56] References Cited

U.S. PATENT DOCUMENTS

| | | | |
|---|---|---|---|
| 4,298,002 | 11/1981 | Ronel et al. | 128/260 |
| 4,309,776 | 1/1982 | Berguer | 3/1 |
| 4,378,016 | 3/1983 | Loeb | 128/260 |
| 4,413,359 | 11/1983 | Akiyama et al. | |
| 4,508,113 | 4/1985 | Malaney. | |

(List continued on next page.)

FOREIGN PATENT DOCUMENTS

| | | |
|---|---|---|
| 0 213 908 | 8/1985 | European Pat. Off. . |
| 0 195 577 A3 | 9/1986 | European Pat. Off. . |

(List continued on next page.)

OTHER PUBLICATIONS

Oxygen Tension Regulates the Expression of Angiogenesis Factor by Macrophages, Knighton et al, Science, vol. 221, Sep. 1983, pp. 1283–1285.

Islet Immuno–isolation: The Use of Hybrid Artificial Organs to Prevent Islet Tissue Rejection, Scharp et., World Journal of Surgery 8, pp. 221–229, 1984.

(List continued on next page.)

*Primary Examiner*—Mickey Yu
*Assistant Examiner*—Choon P. Koh
*Attorney, Agent, or Firm*—McDonnell, Boehnen Hulbert & Berghoff

[57] ABSTRACT

A permeable structure forms a chamber to hold living cells. The structure includes a first permeable region surrounding at least a portion of the chamber having a conformation that, when implanted in host tissue, substantially blocks penetration of host cells into the chamber while permitting solute transport. The structure also includes a second permeable region overlying the first permeable region having a conformation that, when implanted in host tissue, forms a permeable interface with host tissue that permits solute transport. A third permeable region is located between the first and second permeable regions. The third region comprises a solution of polymer material formed in place between the first and second permeable regions. The third permeable region bonds the first and second permeable regions together. The third permeable region also has a conformation that, when implanted in host tissue, permits solute transport between the first and second permeable regions. The third, formed-in-place region bonds the first and second permeable regions together, providing a robust, laminated structure that resists delamination during implantation caused by cellular infiltration into discontinuous spaces between the first and second regions. The third, formed-in-place region can also have a conformation providing an immunoisolation effect. Furthermore, the permeability of the third, formed-in-place membrane is sufficient high that it does not adversely effect the permeability value desired for the overall multiple layer membrane structure.

32 Claims, 13 Drawing Sheets

U.S. PATENT DOCUMENTS

| | | |
|---|---|---|
| 4,664,669 | 5/1987 | Ohyabu et al. . |
| 4,743,252 | 5/1988 | Martin, Jr. et al. . |
| 4,871,366 | 10/1989 | von Recum et al. . |
| 4,936,317 | 6/1990 | MacGregor . |
| 5,024,670 | 6/1991 | Smith et al. . |
| 5,045,205 | 9/1991 | Tyalor ..................................... 210/638 |
| 5,112,614 | 5/1992 | Magruder et al. . |
| 5,156,623 | 10/1992 | Hakamatsuka et al. . |
| 5,213,574 | 5/1993 | Tucker . |
| 5,324,518 | 6/1994 | Orth et al. . |
| 5,344,454 | 9/1994 | Clarke et al. ............................. 623/11 |

FOREIGN PATENT DOCUMENTS

| | | |
|---|---|---|
| 0 259 536 | 9/1986 | European Pat. Off. . |
| 0 259 536 A3 | 3/1988 | European Pat. Off. . |
| 0 359 575 | 3/1990 | European Pat. Off. . |
| WO 83/03536 | 10/1983 | WIPO . |
| WO 88/03785 | 6/1988 | WIPO . |
| WO 89/04655 | 6/1989 | WIPO . |
| WO 910019 | 1/1991 | WIPO .................................... 623/11 |
| WO 92/07525 | 5/1992 | WIPO . |
| WO 93/19700 | 10/1993 | WIPO . |
| WO 93/23154 | 11/1993 | WIPO . |
| WO 94/03126 | 2/1994 | WIPO . |
| WO 94/18307 | 8/1994 | WIPO . |

OTHER PUBLICATIONS

Microtoography and Soft Tissue Response, Campbell et al., Journal of Investigative Surgery, vol. 2, pp 51–73, 1991.

Texturing of Polymer Surfaces at the Cellular Level, Schmidt et al., Biomaterials 1991, vol. 12, May, pp 385–389.

Fibroblast Shape Conformation to Surface Micromorphology, Meyle et al, Journal of Applied Biomaterials, vol. 2, pp 273–276, 1991.

Bulk Chemistry Versus Surface Texture: An in Vivo study of Titanium, Hydrozyapatite, and Silicone, Wu et al, Investigative Surgery 1989:2:51, p. 159.

Cellular Metabolic Activity on Microtextured Silicone, Schmidt et al, Biomaterials; 1991; p. 138.

Surface Characterization ofMicrotextured Silicone, Schmidt et al., Biomaterials; 1991, p. 351.

Influence of Surface Microgemetry on Orientation & Anchorage of Fibroblasts, Meyle et al.

Fibroblast Response to Microtextured Silicone Surfaces: Texture orientation into or out of the surface, Green et al., Journal of Biomedical Materials Research, vol. 28 pp 647–653 (1994).

New Ideas in Biomaterials Science, Ratner, Journal of Biomedical Materials Research, vol. 27, pp 837–850, 1993.

Neovascularization at a Membrane–Tissue Interface is Dependent on Microarchitecture, Pauley et al., Transactions of the Fourth World Biomaterials Congress,Apr. 24–28, 1992, p. 685.

Normal Wound Healing compared to Healing within Porous DacronImplants, Schreuders et al., Journal of Biomedical Materials Researc, VO. 22, pp 121–135 (1988).

Inhibition of Epithelial Downgrowth on Percutaneous Access Devices in Swine, Wasfie et al., Am. Soc. Artif. Intern Organs, vol. XXX, pp 556–560 (1984).

Long–Term Percutaneous Access Device, Freed et al., Trans AM Soc Artif Intern Organs, Vol. XXXI, pp 230–232 (1985).

Effects of a Grooved Epoxy Substratum on Epithelial Cell Behavior in vitro and in vivo, Chehroudi et al., Journal of Biomedical Materials Research, vol. 22 pp 459–473 (1988).

Endothelial Cell Culture on Dacron Fabrics of Different Configurations, Eskin, Journal of Bimedical Materials Research, vol. 12 pp 517–524 (1978).

Physical Characteristics of Expanded Polytetrafluoroethylene Grafts, Boyce, Biologic and Synthetic Vascular Prostheses pp 553–339 (1982).

A Small Arterial Substitute, Campbell et al., Annals of Surgery pp 138–143 (1975).

Expanded Microporous Polytetraflurroethylene as a Vascular Substitute, Campbell et al., Annals of Surgery 85 pp 177–183 (1979).

The Relationship Between Soft Tissue Attachment, Epithelial Downgrowth And Surface Porosity, Squier et al., Journal of Peridontal Research 16: pp 434–440 (1981).

Fabrication and Operation of Polymide Bimorph Actuators for Ciliary Motion System, Ataka et al., Journal of Microelectromechanical Systems, vol. 2, No. 4 Dec. 1993 pp. 146–150.

An Isolation Technology for Joined Tungsten Mems, Yuh–Chen et al., 1993 IEEE pp 189–194.

Fabrication of a Microporous Polyimide Membranes, Nelson et al., IEGG Transactions of Bioengineering (May 1993).

Microfabrication of Porous Polyimide Membranes, Nelson et al., Journal of Biomaterials (May 1993).

High Aspect Ratio Electroplated Microstructures Using A Photosensitive Polyimide Process, Frazier et al., Micro Electro Mechanical Systems '92, Feb. 4–7, 1992 pp 87–92.

Protection of Zenografts with Immunoisolation Membranes, Martinson et al., cellTransplant Society Meeting, May 1–4, 1994.

MULTIPLE-LAYER, FORMED-IN-PLACE IMMUNOISOLATION MEMBRANE STRUCTURES FOR IMPLANTATION OF CELLS IN HOST TISSUE

FIELD OF THE INVENTION

The invention generally relates to systems and methods for implanting materials into body tissue. In a more particular sense, the invention relates to the structures and methods for implanting living cells in host tissue within permeable membrane structures for achieving a desired therapeutic effect, such as, for example, the treatment of diabetes.

BACKGROUND OF THE INVENTION

Many diseases could be treated in a more physiologic fashion if tissue from lower animals could be transplanted into humans. Immunoisolation, as its name implies, is the protection of transplanted organs, tissues, cells, etc. from attack by the host immune system. Isolation from the host immune system is accomplished by the use of a semipermeable membrane.

Recent work by Brauker et al. has demonstrated that a prescribed membrane architecture can promote vascular structures near the host tissue-membrane interface. Such membranes had pores that were formed by membrane structures (strands or fibers) with a diameter of less than 5 $\mu$m, whereas membranes that did not develop near vascular structures had cavities with "plate-like" qualities, having diameters greater than 5 $\mu$m. Histological examination of the vascularizing membranes revealed that the invading inflammatory cells (of the host) had a rounded morphology, while the cells were flattened in the membranes that did not have close vascular structures. See, Brauker et al., Neovascularization of Synthetic Membranes Directed by Membrane Microarchitecture, J. Biomed. Mat. Res., In Press; Brauker, J., Martinson, L., Young, S., Johnson, R. C.: Neovascularization at a membrane-tissue interface is dependent on microarchitecture. Transactions of the Fourth World Biomaterials Congress Apr. 24–28, 1992 p. 685; Brauker, J., Martinson, L., Carr-Brendel, V. E., and Johnson, R. C.: Neovascularization of a PTFE membrane for use as the outer layer of an immunoisolation device. Transactions of the Fourth World Biomaterials Congress Apr. 24–28, 1992 p. 676; Brauker, J., Martinson, L., Hill, R., and Young, S.: Neovascularization of immunoisolation membranes: The effect of membrane architecture and encapsulated tissue. Transplantation 1:163,1992; and Brauker, J., Martinson, L. A., Hill, R. S., Young, S. K., Carr-Brendel, V. E., and Johnson, R. C.: Neovascularization of immunoisolation membranes: The effect of membrane architecture and encapsulated tissue. Transplantation Proceedings 24:2924, 1992; copending Brauker et al. U.S. patent application Ser. No. 08/210,068, filed Mar. 17, 1994, entitled "Close Vascularization Implant Material."

Membranes of the type characterized by Brauker et al. facilitate high levels of vascularization near the membrane-host tissue interface.

Vascularization-promoting membranes of the type characterized by Brauker at el. still must be used in association with an immunoisolation membrane. The immunoisolation membrane is placed between the vascularization membrane and the implanted tissue and has a pore size sufficient to block penetration by host vascular structures completely through the permeable boundary that separates the implanted cells from host tissue. Such penetration breaches the integrity of the boundary, exposing the implanted cells to the complete immune response of the host. Furthermore, the immunoisolation membrane must also prevent the passage of host inflammatory cells (in the case of allografts) and the passage of both host inflammatory cells and molecular immunogenic cells (in the case of xenografts). Vascularization-promoting membranes of the type characterized by Brauker et al., when used in association with an immunoisolation membrane, are capable of supporting allografts at high tissue densities for extended periods, even in the absence of immunosuppressive drugs.

The need for both a vascularization-promoting membrane and an immunoisolation membrane has resulted in laminated membrane structures. For example, Clarke et al U.S. Pat. No. 5,344,454 discloses the lamination of a GORE-TEX™ membrane material (which serves as a vascularization-promoting membrane) and a BIOPORE™ membrane material (which serves as an immunoisolation membrane for allografts) using a criss-crossing pattern of nonpermeable polymeric adhesive. It has been observed that this laminated structure can experience delamination when implanted. This delamination is caused by the infiltration of host inflammatory cells between the two membrane materials, forcing the material apart. This delamination can increase the diffusion distance the laminated membrane structure presents between the host vascular structures and implanted tissue. This, in turn, can adversely effect the passage of nutrients through the laminated membrane structure to the implanted cells.

SUMMARY OF THE INVENTION

One aspect of the invention provides a permeable multiple layer, laminated structure for implanting in host tissue. The permeable structure forms a chamber to hold living cells. The structure includes a first permeable region surrounding at least a portion of the chamber having a conformation that, when implanted in host tissue, substantially blocks penetration of host cells into the chamber while permitting solute transport. The structure also includes a second permeable region overlying the first permeable region having a conformation that, when implanted in host tissue, forms a permeable interface with host tissue that permits solute transport. According to this aspect of the invention, a third permeable region is located between the first and second permeable regions. The third region comprises a solution of polymer material formed in place between the first and second permeable regions. The third permeable region bonds the first and second permeable regions together. The third permeable region also has a conformation that, when implanted in host tissue, permits solute transport between the first and second permeable regions.

The third, formed-in-place region bonds the first and second permeable regions together, providing a robust, laminated structure that resists delamination during implantation caused by cellular infiltration into discontinuous spaces between the first and second regions. The third, formed-in-place region can also have a conformation providing an immunoisolation effect. Furthermore, the permeability of the third, formed-in-place membrane is sufficient high that it does not adversely effect the permeability value desired for the overall multiple layer membrane structure.

Another aspect of the invention provides a permeable structure with a redundant immunoisolation barrier. The structure includes a permeable layer surrounding the chamber that, when implanted in host tissue, blocks contact between cells in the chamber and host cells while permitting transport of solutes. The permeable layer includes a first immunoisolation region having a conformation that, when implanted in host tissue, substantially blocks penetration of host inflammatory cells. The permeable layer also includes a second immunoisolation region distinct from the first region. The second region has a conformation that, when implanted in host tissue, also substantially blocks penetration of host inflammatory cells. The first and second regions are mutually arranged in the permeable layer to together provide a redundant immunoisolation barrier.

In one embodiment, the first and second immunoisolation regions contact each other in the layer. In another embodiment, the first and second immunoisolation regions are spaced apart in the layer.

In a preferred embodiment, the first immunoisolation region is formed in place in contact with the second immunoisolation region by being cast in contact with the second immunoisolation region and then coagulated in place in contact with the second immunoisolation region.

The invention also provides methods for making devices for implanting in host tissue using the permeable structure, as well as methods for implanting living cells within such devices in host tissue.

Other features and advantages of the inventions will become apparent upon review of the following specification, drawings, and claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. The Implant Assembly

Figure 1:
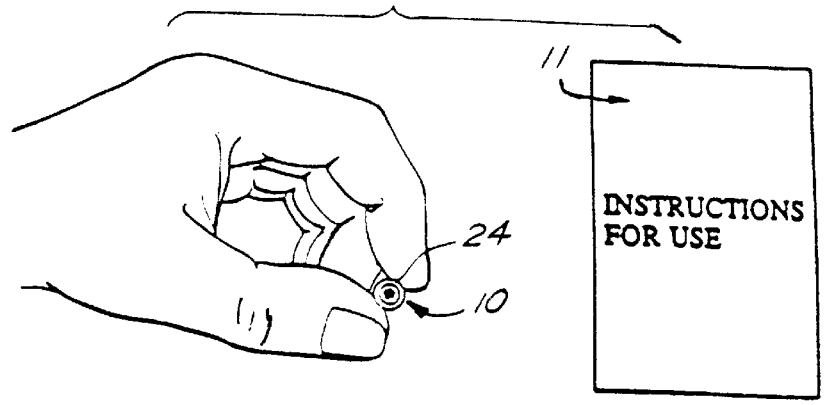
FIG. 1 is a perspective view of an implant assembly that includes a formed-in-place laminated membrane structure that embodies features of the invention, being held in a clinician's hand.
Figure 2:
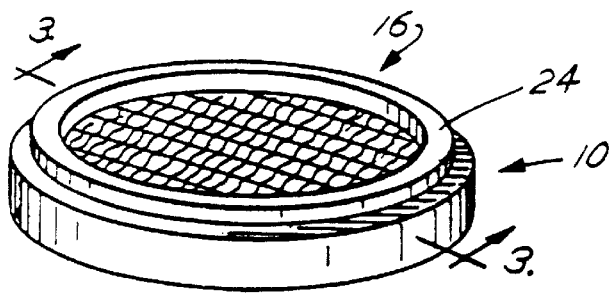
FIG. 2 is an enlarged perspective view of the implant assembly shown in FIG. 1.
Figure 3:
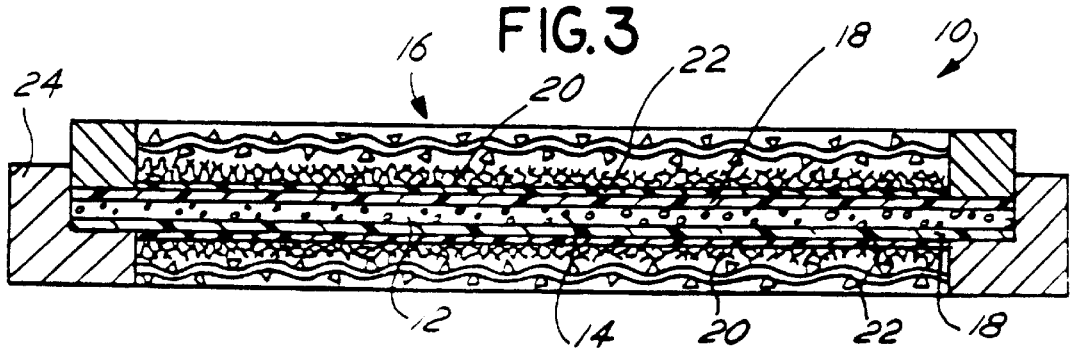
FIG. 3 is a side section view of the implant assembly with formed-in-place laminated membrane structure, taken generally along line 3—3 in FIG. 2.
Figure 2A:
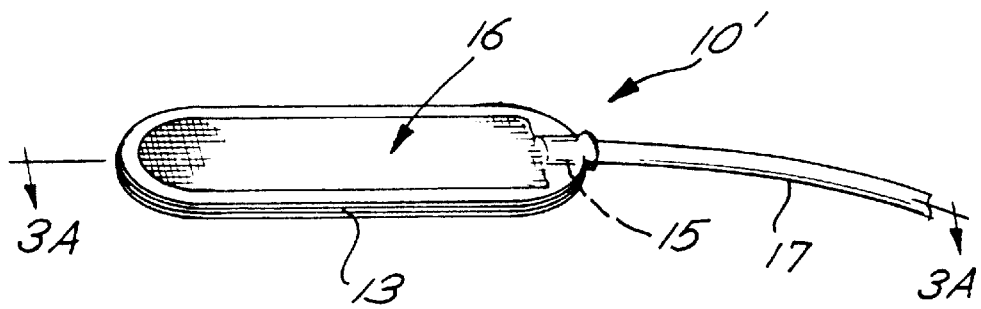
FIG. 2A is an enlarged perspective view of an alternative implant assembly that includes a formed-in-place laminated membrane structure that embodies features of the invention.
Figure 3A:
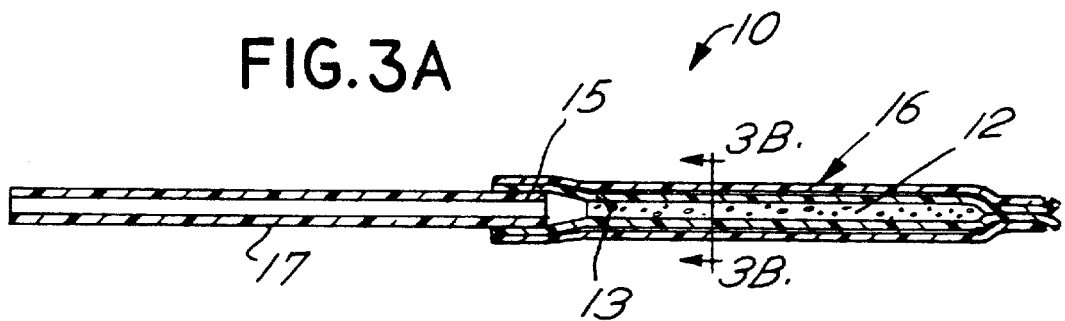
FIG. 3A is a side section view of the assembly shown in FIG. 2A taken generally along line 3A—3A in FIG. 2A.

FIGS. 1 to 3 show one embodiment of an implant assembly 10 that embodies the features of the invention. FIGS. 2A and 3A/B show an alternative embodiment of such an implant assembly 10', which represents a preferred embodiment for reasons set forth below.

Both assemblies 10 and 10' form a chamber 12 (see FIGS. 3 and 3A/B) to hold living cells 14 while implanted in host tissue. The implanted cells 14 generate biological products that the host, because of disease or injury, cannot produce for itself. For example, the chamber 12 can carry clusters of pancreatic cells (called "islets"), which generate insulin for release into and use by a diabetic host.

In the embodiment shown in FIG. 2, the assembly 10 is carried within a hoop-like housing 24. The details of construction of the hoop-like housing 24 are disclosed in U.S. Pat. No. 5,344,454, which is incorporated herein by reference. In the embodiment shown in FIGS. 2A and 3A/13, the assembly 10' comprises a peripherally welded unit, without need for an external housing to lend mechanical support.

The assemblies 10 and 10' each forms a permeable, life sustaining boundary 16 between the implanted cells 14 and the host. The permeable boundary 16 is characterized in terms of its ultimate physical strength and its permeability profile. The boundary 16 serves to isolate the implanted tissue cells from the immune response of the host. The boundary 16 also serves to transfer nutrients and waste products in support of the metabolic processes of implanted cells. The assembly 10' shown in FIGS. 2A and 3A/B includes a sealing or spacing ring 13, to which the peripheral edges of the boundary 16 are sealed by ultrasonic welding.

Regardless of whether the implanted cells 14 are xenogeneic, allogeneic, or isogeneic, the boundary 16 possesses an ultimate strength value that is sufficient to withstand, without rupture, the growth of new vascular structures, the growth of new cells within the chamber 12, and other physiological stresses close to the host tissue. Keeping the boundary 16 secure assures isolation of the implanted cells from both the immunogenic factors and inflammatory cells of the host.

These physiological stresses are caused when the host moves about in carrying out its normal life functions. The proliferation of implanted cells and the growth of vascular structures also contributes to the physiological stresses close to the boundary 16. The stresses challenge the physical integrity of the boundary 16 by stretching or otherwise deforming it. Absent a sufficient ultimate strength value, normal physiological stresses can rupture the boundary 16, exposing the implanted cells to the full effect of the host's immune and inflammatory systems.

The inventors presently believe that ultimate strength values sufficient to withstand physiological stresses close to the host tissue without rupture in animals lie above about 100 pounds per square inch (PSI). The ultimate strength values are determined by measuring the tensile strength of the material. Tensile strength is measured by ASTM D-412.

Also regardless of the type of implanted cell, the boundary 16 must possess a permeability profile that sustains a flux of nutrients into the chamber 12 and waste products from the chamber 12 sufficient to sustain the viability of the implanted cells.

Figure 12:
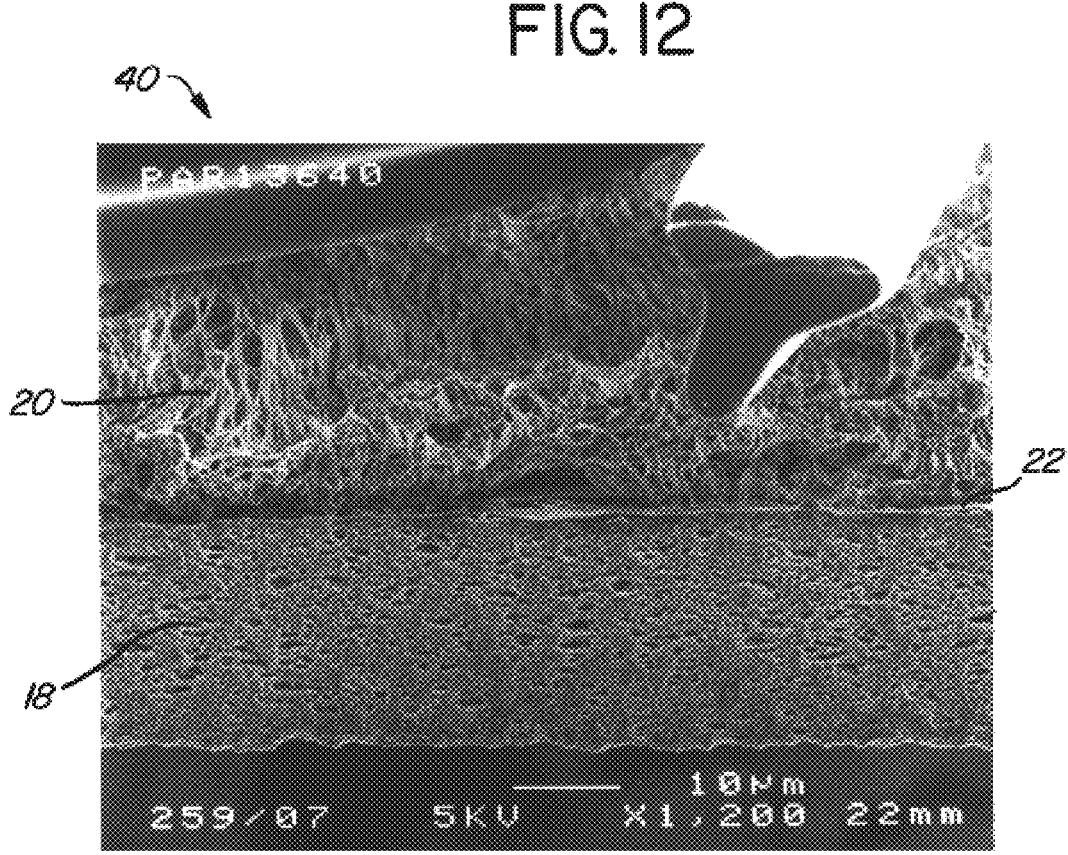
FIG. 12 is a micrograph of a formed-in-place laminated membrane structure that embodies the features of the invention.

Regardless of the particular mechanical configuration of the assembly 10 and 10', in the illustrated and preferred embodiment (which FIGS. 3 and 3A best show), the permeable boundary 16 comprises a first permeable region 18, a second permeable region 20, and a third region 22 between the first and second regions 18 and 20. According to one aspect of the invention, the third region 22 is formed-in-place between the other regions 18 and 20, creating a robust, integrated boundary 16. Furthermore, the parameters for manufacturing the formed-in-place integrated, three-region boundary 16 can also be controlled to provide the permeability profile required to sustain allografts and isografts. As will be pointed out later, FIGS. 3/3A/B and 9 to 11 exaggerate the relative proportions of the various regions 18, 20, and 22 for the sake of illustration. FIG. 12 is an actual micrograph of a formed-in-place laminated structure that embodies the features of the invention, which more accurately shows the relative proportions of the various layers 18, 20, and 22 in a preferred implementation.

The assembly 10' shown in FIGS. 2A and 3A/B represents a preferred embodiment because of the presence of a port member 15, which provides means for accessing the interior chamber 12. An elongated flexible tube 17 extends from the port member 15, through which a syringe can be inserted to place cells in the chamber 12, either before implantation, or after implantation, or to recharge the chamber 12 during implantation. Further details of the construction of the assembly 10' are found in copending U.S. application Ser. No. 08/179,860, filed Jan. 11, 1994.

In the illustrated and preferred embodiment, each assembly 10 10' also includes written instructions 11 (see FIG. 1) that teach the enclosure of living cells within the chamber 12 and the implantation of the chamber 12 with enclosed living cells in host tissue. Exemplary procedures for preparing the device for implanting and for implanting the device with living cells in host tissue are set forth in Section III(c) of this Specification.

A. The First Permeable Region

The first permeable region 18 immediately surrounds the chamber 12 containing the implanted cells 14. The first region 18 possesses multiple characteristics.

Regardless of the type of implanted cell 14 (i.e., xenogeneic, allogeneic, or isogeneic), the first region 18 has a pore size sufficient to block penetration into the lumen of the chamber 12 by host cells. This penetration breaches the integrity of the boundary 16, exposing the implanted cells 14 to the complete immune response of the host. Generally speaking, pore sizes less than about 2 $\mu$m (i.e., 2 micrometers) will block the ingress of vascular structures. As used in this Specification, "pore size" refers to the maximum pore size of the material. The practitioner determines pore size using conventional bubble point methodology, as described in Pharmaceutical Technology, May 1983, pages 36 to 42.

When the implanted cells are from the same animal species but have a different genetic make up (i.e., allografts), the pore size of the first region 18 usually must be sufficient to prevent the passage of inflammatory cells from the host into the implant cell chamber. In allografts, molecular immunogenic factors do not seem to adversely affect the viability of the implanted cells. Still, some degree of tissue matching may be required for complete protection. Pore sizes sufficient to block passage of inflammatory cells in humans lie in the range of below about 0.6 micrometers. These pore sizes, too, are impermeable to vascular structures. As used in this Specification, "inflammatory cells" include macrophages, foreign body giant cells, and fibroblasts, and "molecular immunogenic factors" refers to molecules such as antibodies and complement.

When the implanted cells are isografts (autologous implants of genetically engineered cells), the pore size must be sufficient only to prevent the isografts from exiting the chamber 12, which also prevents ingress of vascular structures in the chamber 12.

In a preferred embodiment, a permeable PTFE membrane material having a thickness of about 25 microns and a maximum pore size of about 0.4 micron is selected for the first region 18. This material is commercially available from Millipore Corporation under the tradename Biopore™. This material has a thickness of about 25 microns and an ultimate (tensile) strength value of at least 3700 PSI, which is well above the desired minimum value. The selected material has a maximum pore size of 0.35 microns, which blocks the passage of inflammatory cells.

It should be appreciated that other, comparable materials can meet the stated requirements for the first region 18. For example, polyethylene, polypropylene, cellulose acetate, cellulose nitrate, polycarbonate, polyester, nylon, and polysulfone materials, cellulose, polyvinylidene difluoride, acrylic, silicone, and polyacrylonitrile can be used.

B. The Second Permeable Region

The second permeable region 20 of the boundary overlies at least a portion of the first region 18. The second region 20 constitutes an interface with host tissue.

In the illustrated and preferred embodiment, the second region 20 has an architecture that promotes the growth of vascular structures in host tissue near the interface. Preferably, at least some of the near vascular structures lie within one cell thickness of the interface.

It is through the second region 20 that the permeable boundary 16 associates itself with the host's biological system closely enough to transfer nutrients and wastes in support of the biological processes of the implanted cells 14. The permeable boundary 16 also transfers the therapeutic products generated by the implanted cells 14 to the host.

Vascularization near the host tissue-boundary interface occurs if the three dimensional conformation of second region 20 promotes certain host inflammatory cell behavior. Brauker et al. have demonstrated that membranes that did have near vascular structures allowed cellular penetration and had pores that were formed by membrane structures (strands or fibers) with a diameter of less than 5 $\mu$m, whereas membranes that did not develop close vascular structures had cavities with "plate-like" qualities, having diameters greater than 5 $\mu$m. Histological examination of the vascularizing membranes revealed that the invading cells had a rounded morphology, while the cells were flattened in the membranes that did not have close vascular structures. The cells appear to be "trapped" and not allowed to flatten on any surface, which apparently causes the more rounded morphology of the cells which infiltrate the vascularizing membranes. The hypothesis is that the membrane architecture dictates cellular morphology, and the rounded cells in turn secrete some, as yet unknown, trophic factors which promote the formation of vascular structures.

Accordingly, the material for the second region 20 is a polymer membrane having an average nominal pore size of approximately 0.6 to about 20 $\mu$m, using conventional methods for determination of pore size in the trade.

Preferably, at least approximately 50% of the pores of the membrane have an average size of approximately 0.6 to about 20 µm.

The structural elements which provide the three dimensional conformation may include fibers, strands, globules, cones or rods of amorphous or uniform geometry which are smooth or rough. These elements, referred to generally as "strands," have in general one dimension larger than the other two and the smaller dimensions do not exceed five microns.

In one arrangement, the material consists of strands that define "apertures" formed by a frame of the interconnected strands. The apertures have an average size of no more than about 20 µm in any but the longest dimension. The apertures of the material form a framework of interconnected apertures, defining "cavities" that are no greater than an average of about 20 µm in any but the longest dimension.

In this arrangement, the material for the second region 20 has at least some apertures having a sufficient size to allow at least some vascular structures to be created within the cavities. At least some of these apertures, while allowing vascular structures to form within the cavities, prevent connective tissue from forming therein because of size restrictions.

Further details of the material are set forth in copending U.S. application Ser. No. 08/210,068 entitled "Close Vascularization Implant Material" filed Mar. 17, 1994, which is incorporated into this Specification by reference.

In a preferred implementation, the second region 20 comprises a membrane material made by W. L. Gore and Associates (Elkton, Md.) under the trade name Gore-Tex™. The Gore-Tex™ material comprises a microporous membrane made from PTFE. The membrane is 15 microns thick and has a pore size of 5 microns.

In another embodiment (not shown), the second region 20 comprises a permeable membrane structure formed with multiple microfabricated layers of polymer film made, for example, from photoimageable polyimide material. The film is processed, using either negative photoresist techniques or etchable membrane fabrication techniques, to create predefined geometric patterns of holes and intermediate spaces defining strands. The geometric patterns alternate between film layers from smaller, more closely spaced hole patterns (with cross hole dimensions equal to or less than about 20 µm and strand dimensions typically about 2–3 µm) to larger holes with less closely spaced patterns (with cross hole dimensions exceeding 20 µm and upwards to about 50 µm and strand dimensions typically about 4–5 µm). The stacking of different geometric patterns creates an open, permeable membrane structure having randomly positioned, interconnected cavities with minimum interior dimensions greater than about 5 µm formed by interconnected stands with minimum dimensions less than about 5 µm.

Further details of this construction are described in copending U.S. application Ser. No. 08/320,199 entitled "Porous Microfabricated Polymer Membrane Structure" filed Oct. 7, 1994, which is incorporated into this Specification by reference.

C. The Third Region

The third region 22 is located between the first and second regions 18 and 20. According to the invention, the third region is formed-in-place between the two other regions 18 and 20. As will be described in greater detail later, the formed-in-place third region 22 can be manufactured from natural or synthetic biocompatible polymers which, when cast, present a permeability and immunoisolation profile comparable to the first region 18.

The preferred embodiment shows the permeable membrane structure being used in association with a chamber for implanting living cells. Still, it should be appreciated that the permeable structure embodying the features of the invention can be used in association with other implanted objects, like catheters, biosensing devices, and the like, which can be carried within the permeable boundary 16 in generally the same fashion as the living cells shown in the drawings.

II. Manufacture of the Permeable Boundary

The permeable boundary 16 functions as a synthetic membrane between host tissue and the cells 14 contained in the chamber 12. With a concentration gradient as the driving force, the boundary membrane permits the selective transport of certain molecular solutes between host tissue and the cells 14, while blocking the transport of other molecular solutes. The nature of the transport and blockage functions depends on prescribed, discriminating interactions between the physical configuration of the membrane and the physical configuration of the transported material. For synthetic membranes these interactions are based for the most part on the size of the transported material relative to the size and distribution of the passageways or pores within the membrane. In synthetic membranes, the size of the membrane pores often varies, sometimes over a broad range. In addition, the diffusion process within the various membrane pores can be significantly hindered relative to that in free solution by interactions of the solute with the pore walls, even when the solute is several times smaller than the pore.

The criteria in developing an immunoisolating membrane includes the creation of a structure for which (i) the largest pore will prohibit passage of a defined type or types of solute, and (ii) the distribution of pore size has a mean sufficiently close to the maximum pore size so that the diffusion of the desired small solutes is not overly hindered by a large population of very small pores.

The third region 22 is made by a process of controlled phase change, called "casting," in which the membrane material, a high molecular weight synthetic polymer, is first dissolved in a solvent, then applied upon the either one of the first or second permeable region 18 or 20, with the other permeable region then laid on top, and then exposed to conditions which cause the material to precipitate from solution in a macroscopically continuous phase on the third region 22. Careful selection and control of membrane material, solvent system, concentration, and phase inversion conditions determine the final membrane micro-architecture and permeability.

The polymer material for the third region 22 can comprise a natural or synthetic polymer selected based upon considerations that include its biocompatibility, its ease of fabrication, its ability to consistently form predictable, identifiable geometries and distributions, its chemical inertness, and its strong mechanical properties. For example, poly (ethylene-co-vinyl alcohol) (EVOH) is a polymer that meets the above criteria. However, it should be appreciated that other natural and synthetic polymers, for example, cellulose acetate (CA), poly(vinylidene difluoride) (PVDF), and ethyl vinyl alcohol (EVA) meet these criteria, as well, as do silicone, ceramic materials, and other elastomer and thermoplastic materials.

FIGS. 4 to 11 show the steps in the casting process performed in accordance with the invention. These steps are performed, regardless of the particular polymer selected.

The membrane casting process is preferably carried out in an enclosed casting chamber 24 (see FIG. 4) beneath a standard laboratory fume hood. The casting chamber 24 permits the continuous flow of filtered air over the casting area.

Present within the casting chamber 24 (see FIG. 5) are a casting plate 26, a casting blade 28, a syringe 30 containing dissolved polymer dope, a quenching bath 32, and a rinsing bath 34. The first and second membrane regions 18 and 20 are also handled within the casting chamber 24.

The casting plate 26 is preferably polished stainless steel, but it can also be mirror glass. Its dimensions can vary. In one representative embodiment, the casting plate 26 (including an associated stretching frame) measures 6.4 inch by 10.1 inch, with a thickness of about 0.25 inch.

The plate 26 is cleaned, either with Contrad 70 (Curtin-Matheson Scientific) for steel or Chromerge (Mallinckrodt) for glass, rinsed thoroughly, dried in open air, flushed with filtered air, and then placed immediately into the casting chamber 24.

Figure 5:
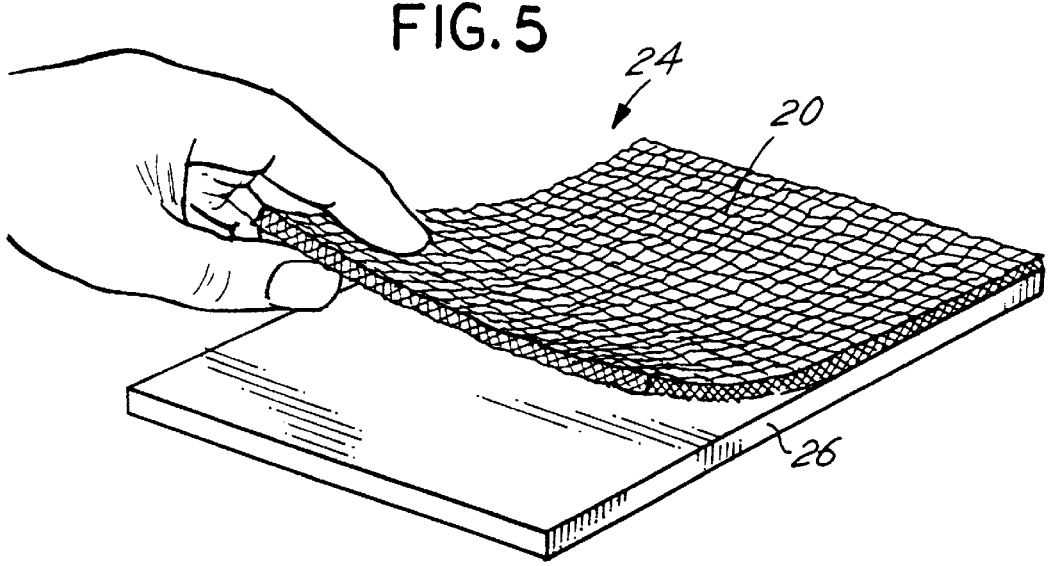
FIGS. 5 to 11 show the steps in manufacturing the formed-in-place laminated membrane structure using the apparatus shown in FIG. 4.
Figure 6:
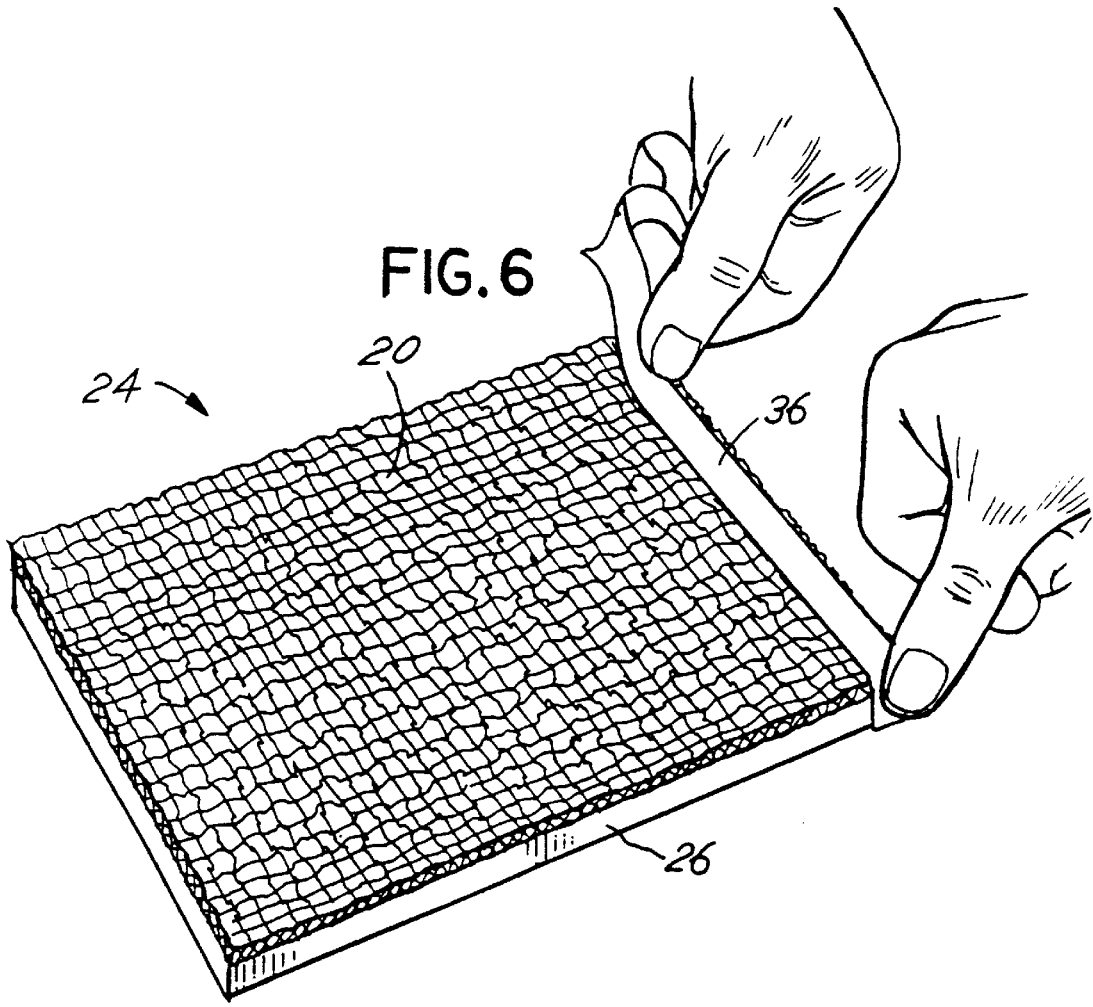

Referring now to FIGS. 5 and 6, the second permeable region 20 (for example, the GORE-TEX™ material described above) is peripherally secured to the casting plate 26 within the casting chamber 24, using tape 36, adhesive, or both. The side of the region 20 which, when implanted, faces implanted host tissue lies face down on the casting plate 26. It is important that the second region 20 lays in intimate surface contact against the entire casting plate 26, and that the region 20 is free of wrinkles. In this regard, it may be necessary to first stretch the region 20 on a stretching frame (not shown) before placing it on the plate 26. The casting plate 26 may also be made with a slightly convex surface to assure intimate surface contact, particularly between the midportion of the plate 26 and the second region 20.

The syringe 30 contains the polymer material selected for the third region 22, which is dissolved in dope form in a selected solvent. The details of the dissolution process will vary according to the polymer used.

For example, EVOH is available in various molecular weights and monomer ratios from EVAL Company of America. The E-series material, containing 44 mole % ethylene, is used; however, other mole % ethylene EVOH materials can be used. To make a suitable batch, a desired weight percent of the EVOH material is weighed out into a small bottle. A desired weight percent of polyvinylpyrrolidone (PVP) is added to achieve the desired viscosity. An organic solvent like dimethylsulfoxide (DMSO) is added to make up the remaining weight percent. The solids are allowed to dissolve as the bottle is rotated at room temperature. Rotation assures proper adhesive dissolution and uniformity. The bottle is rotated until all solids are dissolved, typically up to 20 hours. Concentrations of from about 3 wt % to 8 wt % EVOH and from 2 wt % to 8 wt % PVP are recommended to serve as the formed-in-place third region 22. Other higher or lower weight percentages can be used, depending upon processing conditions. After complete dissolution, the solution is cooled and pressure filtered prior to use.

After dissolution, the polymer dope is drawn up into the syringe 30 (which can be a 5 cc polypropylene syringe manufactured by Becton-Dickinson). The syringe 30 is capped, flushed with filtered air, and quickly placed in the casting chamber 24.

Figure 7:
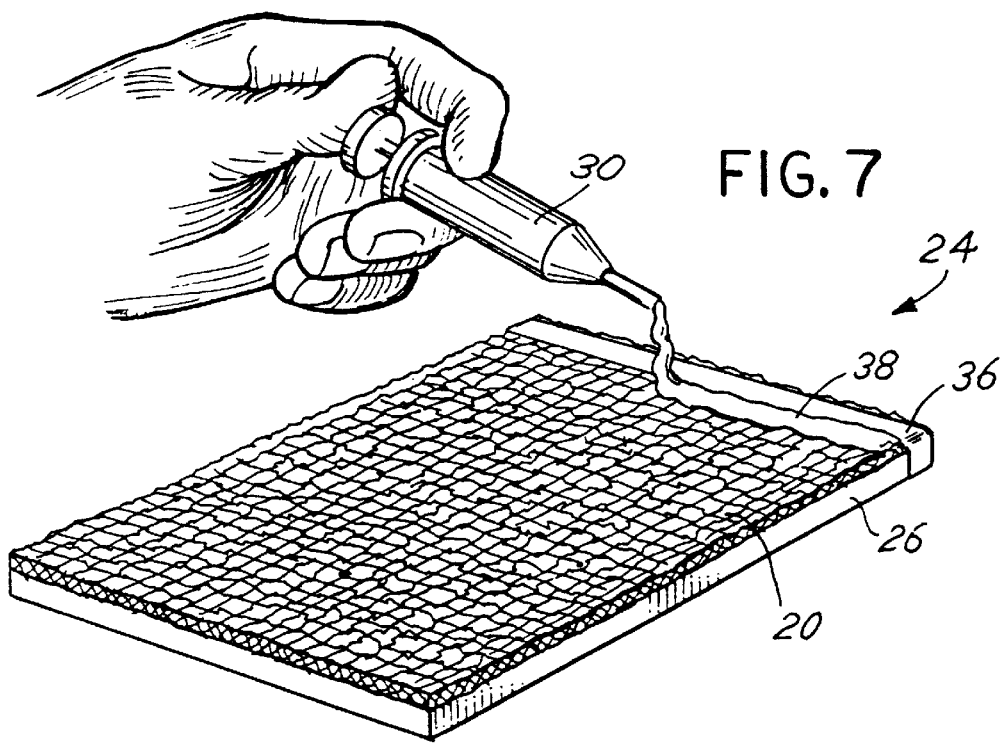
Figure 8:
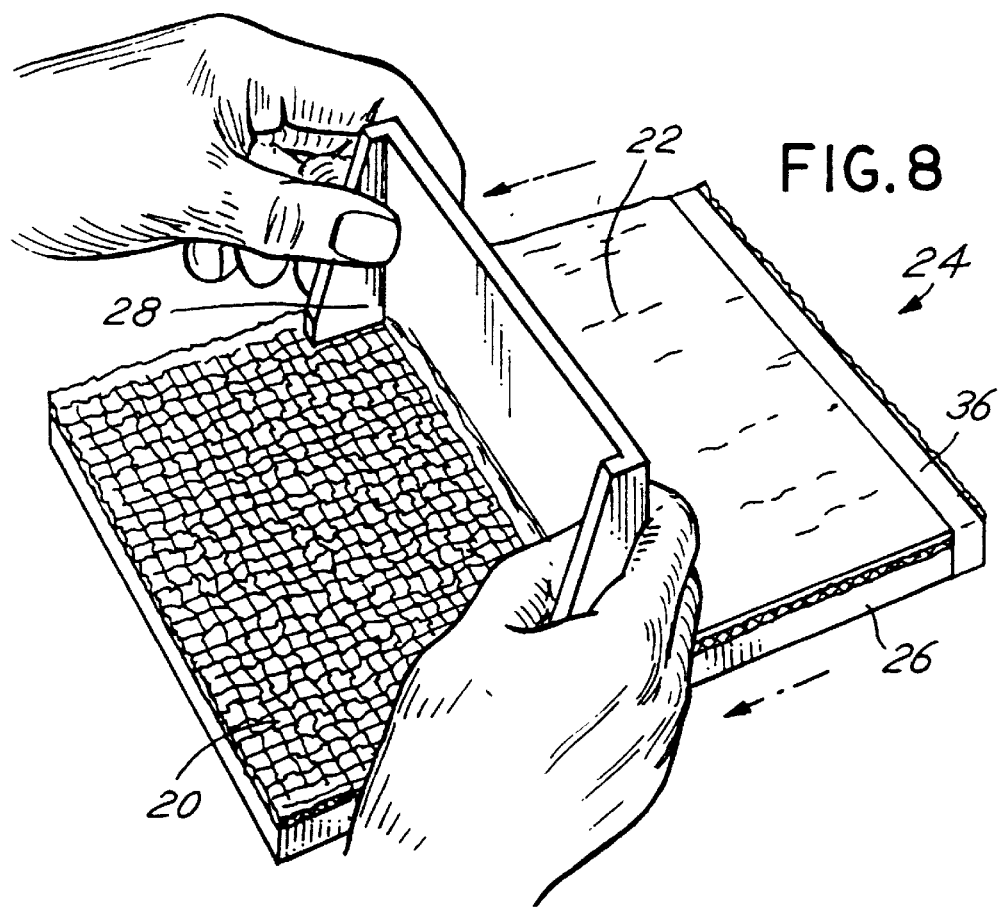

As FIG. 7 shows, within the casting chamber 24, the polymer dope is manually dispensed from the syringe 30 in an elongated bead 38 (typically about ⅛-inch in diameter, or about 1 to 2 cc) along the upper portion of the second region 20 on the casting plate 26. As FIG. 8 shows, the dope bead 38 is then spread out or "drawn down" over the surface of the second region 20 by slowly dragging the casting blade 28 along the length of the plate 26 at a steady rate of about 10 to 20 inches per minute.

The thickness of the dope drawn down on the second region 20 depends upon the size of the gap that separates the edge of the casting blade 28 from the exposed surface of the second region 20. The size of the gap can vary between depending upon the polymer used and the thickness desired. Using EVOH polymer dope, a gap of between 1.0 to 5.0 mil is recommended.

It is desirable that a portion of the polymer dope actually penetrates the surface of the second region 20 to some extent. This penetration further enhances the presence of a secure, physical bond to hold the first and second regions 18 and 20 together. Depending upon the surface tension characteristics of the second region 20 and the cast polymer used, it may be necessary to pretreat the second region 20 with a water soluble surfactant like FC-135, Pluronic, or Triton X100, before applying the dope bead. Other fluorosurfactants can be used. The pretreatment controls the adhesion and depth of penetration of the drawn-down dope by altering the hydrophility of the second region 20. For example, pretreating the PTFE surface of a GORE-TEX material with a 0.1% to 0.2% FC-135 solution can be accomplished before casting with an EVOH polymer, although it is believed that such pretreatment is not critical to the overall process when using an EVOH polymer.

The desired degree of penetration can be controlled by balancing between the viscosity of the polymer dope (controlled by adding PVP) and the surface characteristics of the second region 20 (controlled by using surfactant and the like).

Figure 9:
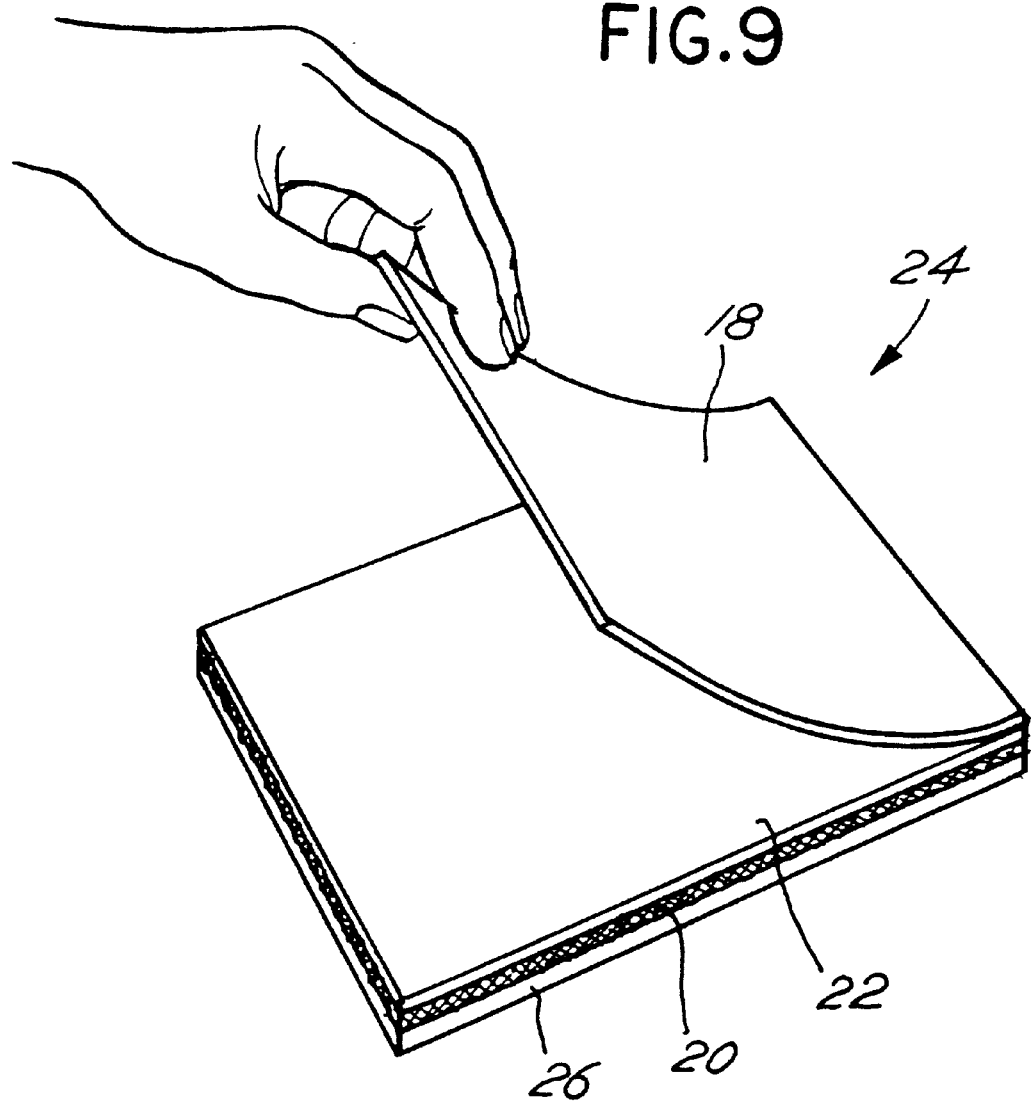

As FIG. 9 shows, once the polymer dope has been drawn down along the entire second region 20, the first region 18 (for example, the BIOPORE™ material described above) is laid upon the casting plate 26 in intimate contact with the drawn-out dope polymer region 22. The drawn down dope polymer region 22 will tend to stick immediately upon contact with the first region 18. For this reason, it is recommended that a plastic film (such as PP2500 transparent film sold by 3M) be laid on top of the first region 18, so that a smooth, consistent pressure against the first region 18 can be applied, starting with initial contact at the center and working from there outward. As the entire first region 18 is wetted out in the dope polymer, the plastic film can be removed.

Figure 10:
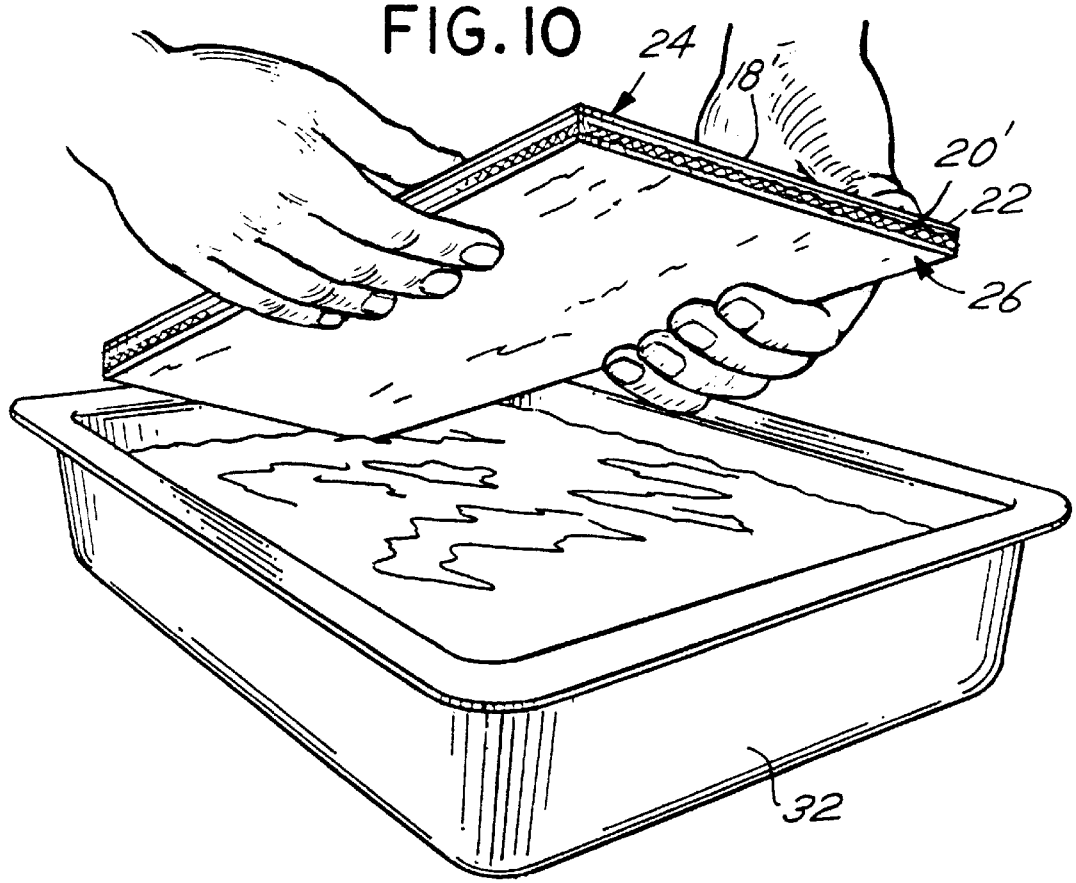

Once the tri-layer laminate 40 is assembled on the casting plate 26 (as FIG. 10 shows), the casting plate 26 is lifted and slid smoothly into the quenching bath 32. The contents of the quenching bath 32 will vary according to the polymer used. For EVOH polymer, the quenching bath 32 can comprise ethanol (EtOH), or reagent alcohol (RA), or water (H2O), or mixtures of water and DMSO (the recommended ratio being 75% H2O and 25% DMSO). Other solvent systems can be used. The quenching bath 32 is preferably maintained at a temperature of between 20° C. and 25° C. when EVOH polymers are being cast. Depending upon the solvent system and the permeability desired, the temperature range can vary.

The EVOH polymer is insoluble in the quenching bath 32, whereas the PVP, organic solvent, and penetrating agents like surfactant are all soluble in the bath 32. The permeable structure of the third region 22 thus forms in the quenching bath 32. The bond between the third region 22 and the first and second regions 18 and 20 also forms in the quenching bath 32. The permeable structures prepared from the polymer solutions, as above described, can be broadly classified as hydrogels in the sense that, in the presence of water, they form highly solvated, three dimensional, permeable networks with local regions of close molecular association which provide strength to the network.

Figure 11:
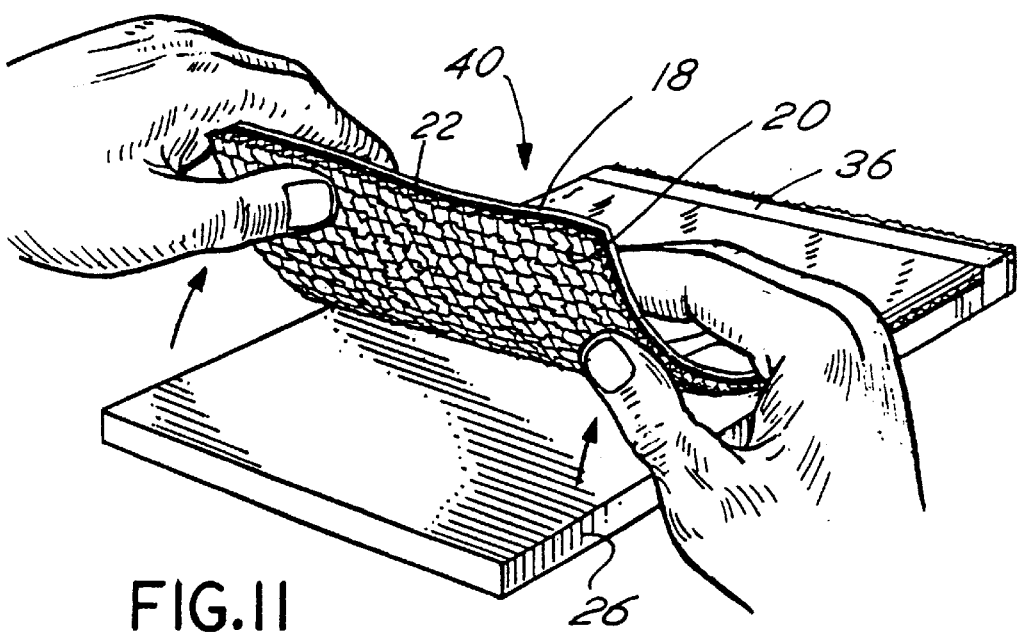

After a prescribed period of time (usually at least 30 minutes), the plate 26 and tri-layer cast laminate 40 are removed as a unit from the quenching bath 32. The tri-layer cast laminate 40 is gently removed from the casting plate 26, as FIG. 11 shows. It is then allowed to float freely in a water wash bath 34 for a prescribed period of time (usually for 20 to 24 hours) to remove fillers, organic solvents, and penetrating agents. The temperature of the wash bath 34 is maintained at a temperature of about 37° C., however other temperatures can be used.

After washing, the tri-layer cast laminate structure 40 is carefully laid out and allowed to dry, at least overnight, before testing or use.

It should be appreciation that alternative methods could be used to apply the polymer dope.

In one alternative process (not shown), the dope bead 38 can be applied and drawn down directly on the first region 18 using the casting blade 28, and the second region 20 laid on top. The tri-layer structure 40 is then placed in the quenching bath 32, as previously described, followed by the subsequent water bath 34, and drying, also as previously described.

In another alternative process (also not shown), the polymer dope can be applied without using a casting blade. In this process, a screen or template can be dipped in the polymer dope material and then laid upon the second region 20. The dipped screen deposits a predetermined pattern of the polymer dope on the surface of the second region 20, which remains upon removal of the screen. The first region 18 is then laid on top of the polymer dope pattern. The resulting tri-layer structure 40 is then placed in the quenching bath 32, as previously described, followed by the subsequent water bath 34, and drying, also as previously described.

Figure 17:
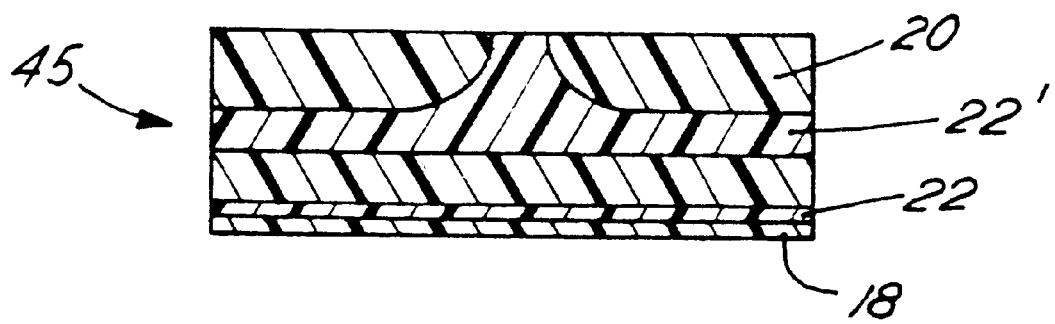
FIG. 17 is a side section view of a redundant immunoisolation barrier that embodies the features of the invention.

It should also be appreciated that, by controlling the viscosity of the polymer dope (controlled by adding PVP) and the surface characteristics of the second region 20 (controlled by using surfactant and the like), as previously described, the polymer dope can be made to actually penetrate deeper into the permeable second region 20 (see FIG. 17). Subsequent quenching, as already described, creates a formed-in-place permeable region 22' located within the second region 20 (as FIG. 17 shows). The sub-surface region 22' can itself serve as an immunoisolation barrier imbedded within the permeable region 20, without the addition of the first region 18 or its equivalent. Alternatively (as FIG. 17 shows), the first region 18 or it eqivalent can also be affixed to the surface of the second region 20, this time using a formed-in-place region 22 to laminate the first and second regions 18 and 20 together, or by some other lamination method.

Figure 3B:
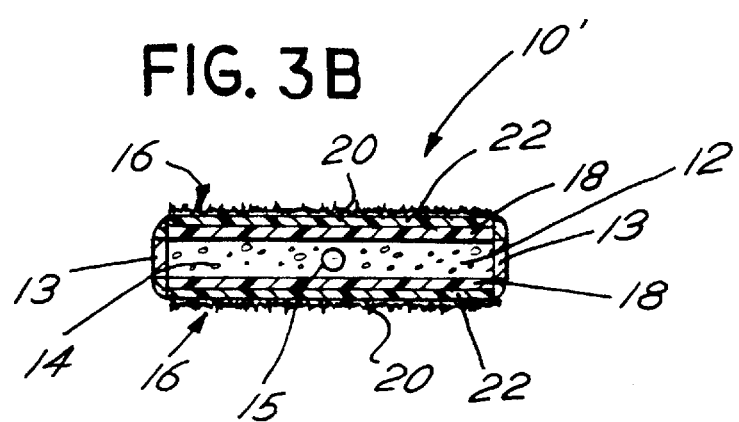
FIG. 3B is an enlarged end section view of the assembly shown in FIG. 2A, taken generally along line 3B—3B in FIG. 3A.
Figure 4:
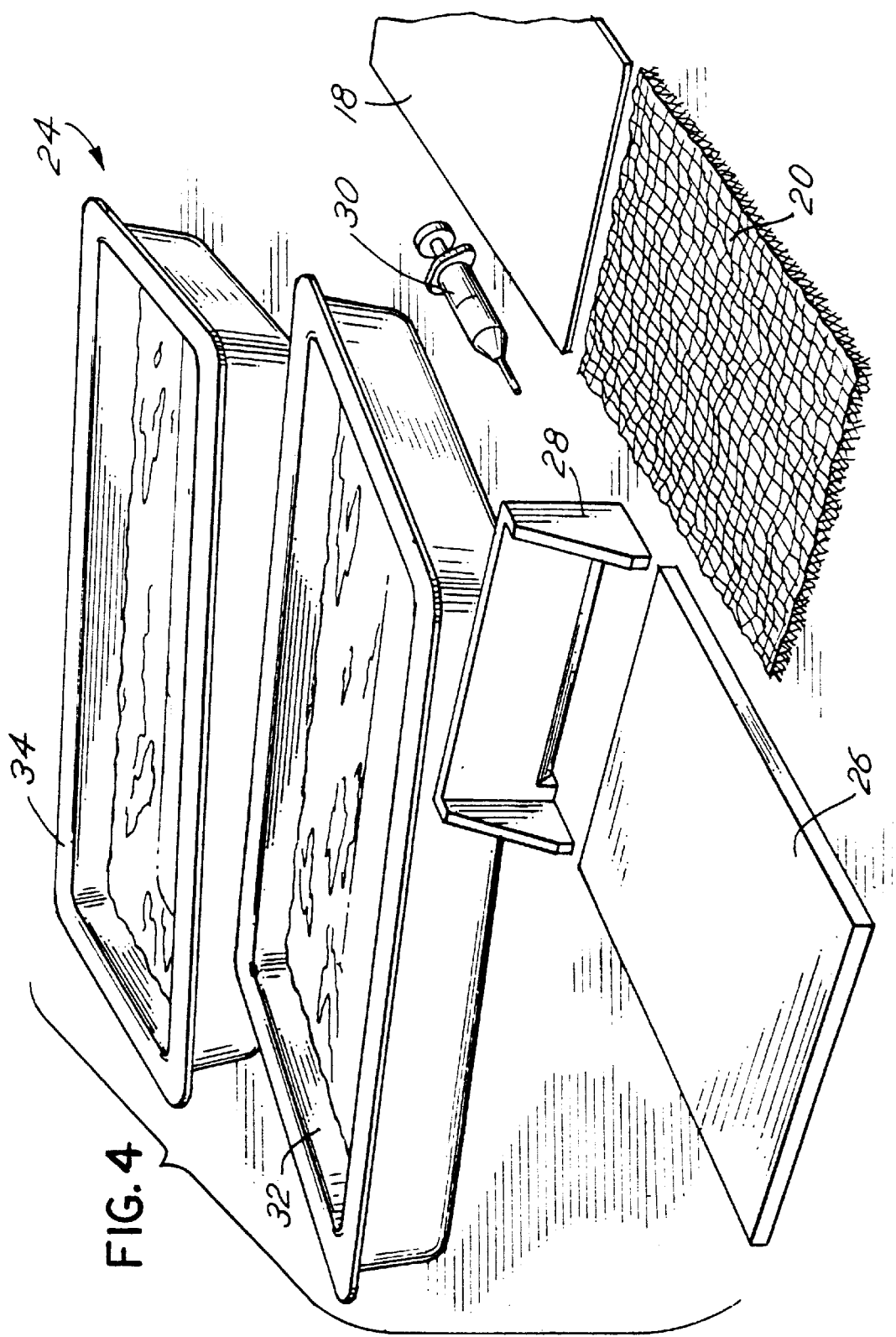
FIG. 4 is a perspective view of a casting chamber containing apparatus used to manufacture formed-in-place laminated membrane structures that embody features of the invention.

The formed-in-place region can be located either on the surface of the second region 20 (as region 22), where it serves also to bond the immunoisolation first region 18, or within the second region 20 (as region 22') spaced away from the first region 18. By tailoring the permeability of the formed-in-place regions 22 and 22' to block penetration of host inflammatory cells, the invention makes possible the creation of a redundant immunoisolation barrier 45, comprising multiple immunoisolation regions or layers 18, 22', and (optionally) 22. It should also be appreciation that the barrier 16 shown in FIGS. 3 and 3B can also include redundant immunoisolation barriers, if the region 22, like the region 18, has a conformation that substantially blocks penetration of host inflammatory cells. The region 22 backs up the immunoisolation function of the first region 18, and vice versa, in case of a manufacturing problem, failure due to handling, or while implanted. The invention therefore makes possible a redundant immunoisolation function without adversely affecting the overall permeability of the overall permeable structure.

III. Characterizing the Cast Laminated Structure

A. Morphology

FIG. 12 shows an actual micrograph of a representative tri-layer cast laminate 40 made according to the above-described process, examined using FE LVSEM analysis. The laminate 40 comprises 5 μm GORE-TEX™ material as the second region 20; 0.4 μm BIOPORE™ PTFE material as the first region 18; and a formed-in-place polymer comprising EVOH (3 wt % EVOH; 2% PVP; quenched in 100% ethanol) as the third region 22. Analysis reveals that the formed-in-place EVOH layer 22 typically ranges from approximately 0.1 to 1.25 μm in thickness, but can be as much as 200 μm (it should thus be appreciated that preceding FIGS. 3 and 9 to 11 exaggerate the relative proportions of the various regions 18, 20, and 22 for the sake of illustration). As FIG. 12 shows, the cast EVOH layer 22 is typically also in substantially continuous, intimate contact with both the first and second regions 18 and 20, and is sometimes observed to penetrate into both facing first and second regions 18 and 20 to a depth of several micrometers.

B. Permeability

Stirred diffusion cell and multi-solute permeability testing further reveals that the presence of the continuous formed-in-place layer 22 does not significantly reduce the overall permeability of the laminate to Tryptophan (Sigma T-0254) (0.5 mg/ml), Molecular Weight 204.2 D ; Vitamin $B_{12}$ (Sigma V-2876) (1.5 mg/ml), Molecular Weight 1355 d; Myoglobin (Sigma M-0630) (6 mg/ml), Molecular Weight 17,000 d; Albumin (Sigma A-8022) (22 mg/ml), Molecular Weight 65,000 d; and IgG (Sigma I-5506) (25 mg/ml), Molecular Weight 160,000 d.

The following table lists the permeabilities of laminates of 0.4 μm BIOPORE™ PTFE material (abbreviated B in the Table) (comprising the first region 18); a variety of EVOH formed-in-place polymers ranging between 3 wt % and 8% EVOH, blade gaps of 1.4 mil/2.8 mil/4.2 mil, and quenching baths comprising either EtOH or water (H2O) (comprising the third region 22) (designated E-EtOH or E-H2O, depending upon the quenching bath); and 3 μm or 5 μm GORE-TEX™ materials (abbreviated G5 or G3) (comprising the second region 20). The control laminate comprised 0.4 μm BIOPORE™ PTFE material laminated to 5 μm GORE-TEX™ material using EVA strands, as disclosed in U.S. Pat. No. 5,344,454. Permeabilities are express in terms of $cm/sec \times 10^{-4}$. Sample size is abbreviated S(n).

TABLE 1

Permeability of Cast Laminated Structures
(All values are x $10^{-4}$ cm/sec)

| Laminate | L-Tryp | $B_{12}$ | Myo | Alb | IgG |
|---|---|---|---|---|---|
| Control (S1) | NA | 1.59 | 0.56 | 0.31 | 0.22 |
| B/E-EtOH/5G (S52) | 3.26 ± 0.53 | 1.83 ± 0.27 | 0.64 ± 0.09 | 0.35 ± 0.07 | 0.24 ± 0.06 |
| B/F-H2O/G5 (S12) | 3.40 ± 0.16 | 1.80 ± 0.13 | 0.59 ± 0.04 | 0.30 ± 0.03 | 0.21 ± 0.03 |

Figure 13:
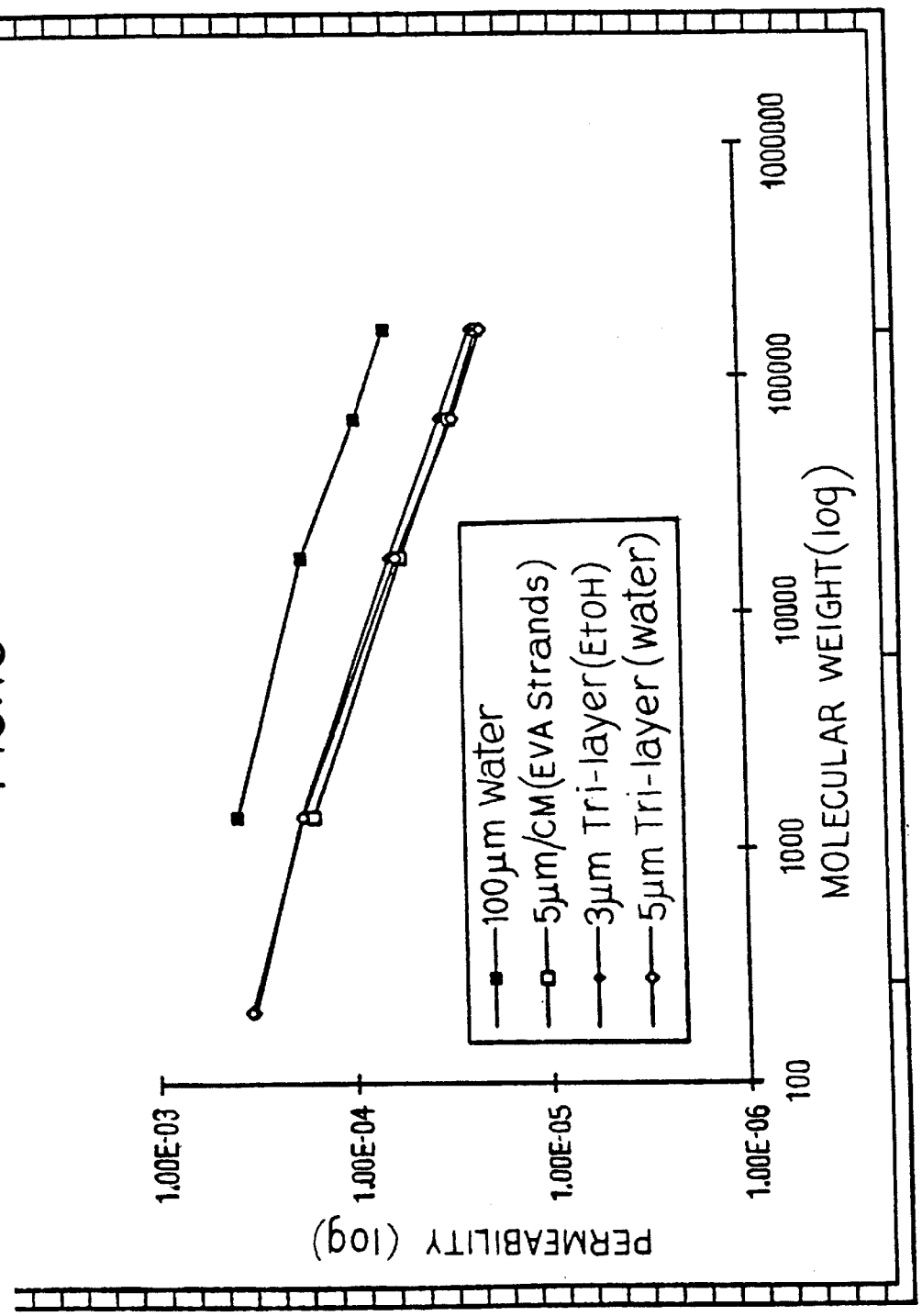
FIG. 13 is a log graph comparing the permeability of formed-in-place laminated membrane structures embodying the invention to a prior laminated membrane structure.

FIG. 13 is a log-graph that compares the permeability over a range of molecular weight solutes of the various cast laminates to the control and to 100 μm water. FIG. 13 demonstrates that the cast tri-layer laminates made according to the invention are comparable to the control, which is known to possesses a range of permeabilities suited for at least allografts and isografts. FIG. 13 also demonstrates that the presence of the third region to bond the first and second regions together, does not significantly alter the permeability characteristics of the overall composite structure. In fact, Table 1 demonstrates that using the formed-in-place region, establishing intimate surface contact with the other regions, actually improves the permeability, compared to using EVA strands as the bonding agent (i.e., the control material).

Although the actual permeability of the formed-in-place layer 22, $k_{m,22}$, cannot be measured directly, it can be estimated from the independently measured permeabilities of the adjacent layers 18 and 20 using the series mass transfer relationship:

$$\frac{1}{k_{m,22}} = \frac{1}{k_{m,40}} - \frac{1}{k_{m,18}} - \frac{1}{k_{m,20}}$$

where $k_{m,40}$, $k_{m,18}$, and $k_{m,20}$ are, respectively, the permeabilities of the laminate 40, the second region 18, and the first region 20. Using an average vitamin $B_{12}$ value from Table 1 of $1.82 \times 10^{-4}$ cm/sec for $k_{m,40}$, and values for $k_{m,18}$ and $k_{m,20}$ of, respectively, $4.65 \times 10^{-4}$ cm/sec and $3.75 \times 10^{-4}$ cm/sec (obtained from separate studies), $k_{m,22}$ is found to be $14.8 \times 10^{-4}$ cm/sec, over eight times the permeability of the entire laminate 40.

C. Implantation Studies

Laminate 40 were formed using the above described methodology comprising 0.4 μm BIOPORE™ PTFE material as the first region 18; a cast-in-place third region 22 comprising 3 wt % EVOH, 8 wt % PVP, 2% surfactant, cast using a 2.8 mil blade gap; and 5 μm GORE-TEX™ material as the second region 20. The following Table 2 lists the permeability of the laminate 40 (six samples).

TABLE 2

Permeability of Implanted Cast Laminate
(All values are x $10^{-4}$ cm/sec)

| L-Trp | $B_{12}$ | Myo | Alb | IgG |
|---|---|---|---|---|
| 2.7612 ± 0.2692 | 13588 ± 0.0778 | 0.2690 ± 0.0340 | 0.0624 ± 0.0166 | 0.0335 ± 0.0131 |

The six samples were formed into six ported devices of the configuration shown in FIGS. 2A and 3A/B, each having a 20 μl chamber for implanting living cells in host tissue. Ported devices were also made with the control membrane described above in connection with Table 1. The ported devices were assembled and sterilized with an overnight soak in 70% ethanol.

A first group of the devices made with the laminate 40 were implanted in the epididymal fat pads of Lewis rats, as were comparable devices made with the control membrane. In this group, the chambers were empty. This group will be called Group 1.

A second group of the devices made with the laminate 40 were implanted in epididymal fat pads of Lewis rats, as were comparable devices made with the control membrane. In this group, the chambers were filled via the port 15 with the same human fibroblast cell line. This group will be called Group 2, which comprised xenografts.

A third group of the devices made with the laminate 40 were implanted in epididymal fat pads of athymic (immune compromised) rats, as were comparable devices made with the control membrane. In this group, the chambers were filled via the port 15 with the same human fibroblast cell line. This group will be called Group 3.

The implants were removed after three weeks. Explanted devices were prepared for histology by standard methods and stained with hematoxylin and eosin. Sections were scored by three criteria:

(I) Tissue Survival within the Device (Tissue Score) (1=no survival to 6=healthy, well differentiated epithelial tissue).

(ii) Host Response Outside the Device (Host Reaction) (1=low level reaction to 6=high reaction, macrophages and lymphocytes and plasma cells).

(iii) Membrane Delamination (Delamination), derived by measuring, for each device, the total linear distance about the midsection of each device (DTOT) and the linear distance in which the first and second regions of the associated membrane were separated by more than one cell layer (about 15 μm) (DSEP). Delamination is expressed as a percentage by dividing DSEP by DTOT.

The following Table 3 lists the histology results.

TABLE 3

Histology Results

| Device | Tissue Score | Host Reaction | Delamination |
|---|---|---|---|
| Group 1 Control | NA | 1.9 ± 0.5 | 20.9 ± 7.2 |
| Group 1 Cast | NA | 2.0 ± 0.4 | 4.9 ± 0.9 |
| Group 2 Control | 2.0 ± 0.0 | 5.8 ± 0.5 | 32.3 ± 11.5 |
| Group 2 Cast | 1.0 ± 0.0 | 4.4 ± 0.2 | 6.2 ± 3.2 |
| Group 3 Control | 4.0 ± 0.0 | 2.2 ± 0.3 | 13.7 ± 5.8 |
| Group 3 Cast | 4.0 ± 0.0 | 2.1 ± 0.2 | 6.8 ± 4.3 |

The Group 1 and Group 2 and Group 3 results all demonstrate that the host reaction to the cast laminate material is comparable to the host reaction to the control material, either without living cells and with living cells. The presence of the laminate region 22 does not itself create an added host response.

The Group 3 result demonstrates that the tissue scores for the cast laminate material are also comparable to the tissue scores for the control material. The presence of the laminate region does not effect the ability of the device to sustain living cells in host tissue.

The Group 1 and Group 2 and Group 3 results all demonstrate the superior resistance that the cast laminate material has to delamination, compared to the control membrane. Even in the presence of a strong host response (Group 2 xenografts), the cast laminate significantly reduced the incidence of delamination, compared to the control membrane.

Figure 14:
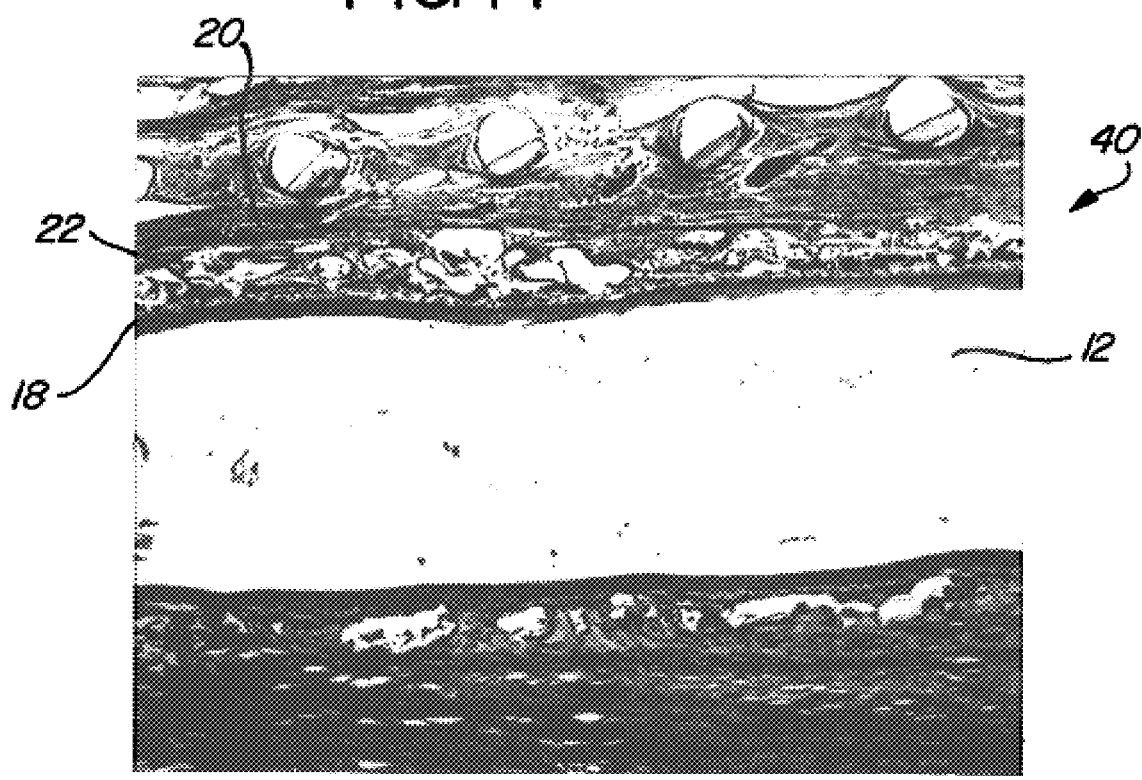
FIG. 14 is a micrograph of a formed-in-place laminated membrane structure after implantation in host dog tissue for ten weeks, showing the absence of delamination.
Figure 15:
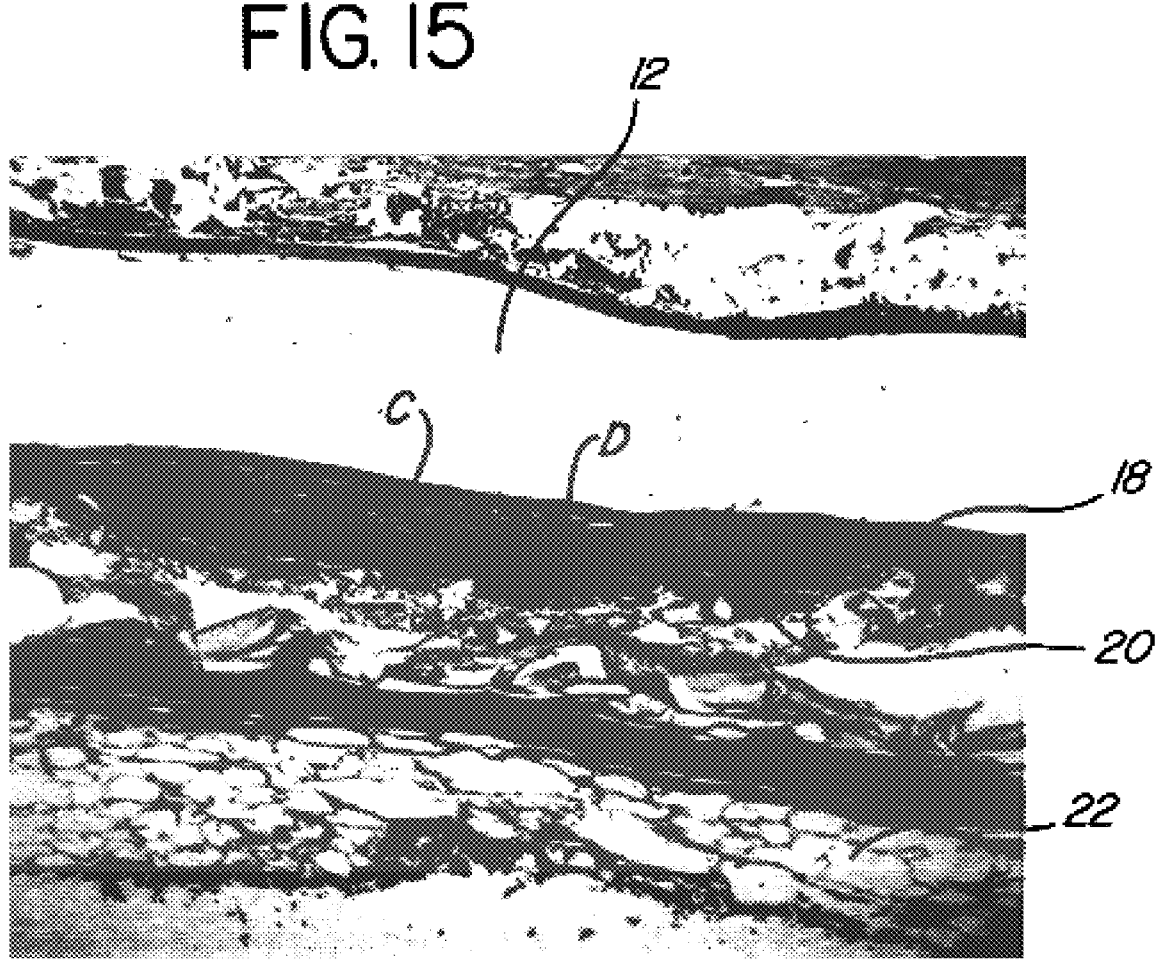
FIG. 15 is a micrograph of a prior laminated membrane structure after implantation in host dog tissue for ten weeks, showing the presence of delamination.

FIG. 14 is an actual micrograph of a tri-layer cast laminate 40 made according to the invention after 10 weeks of implantation (without living cells) in a dog. FIG. 15 is a micrograph of the control membrane after 10 weeks of implantation (without living cells) in a dog. FIG. 14 shows the absence of delamination of the tri-layer cast structure, while FIG. 15 shows the presence of delamination in the control membrane structure, the area of delamination being indicated by the letter D in FIG. 15. The cause of the delamination in FIG. 15 is the infiltration of host cells (indicated by the letter C in FIG. 15) between the first and second regions 18 and 20. FIG. 14 shows that the robust, integrated nature of the tri-layer cast laminated structure resists cellular infiltration into the formed-in-place third region, thereby preventing delamination of the overall boundary.

Figure 16:
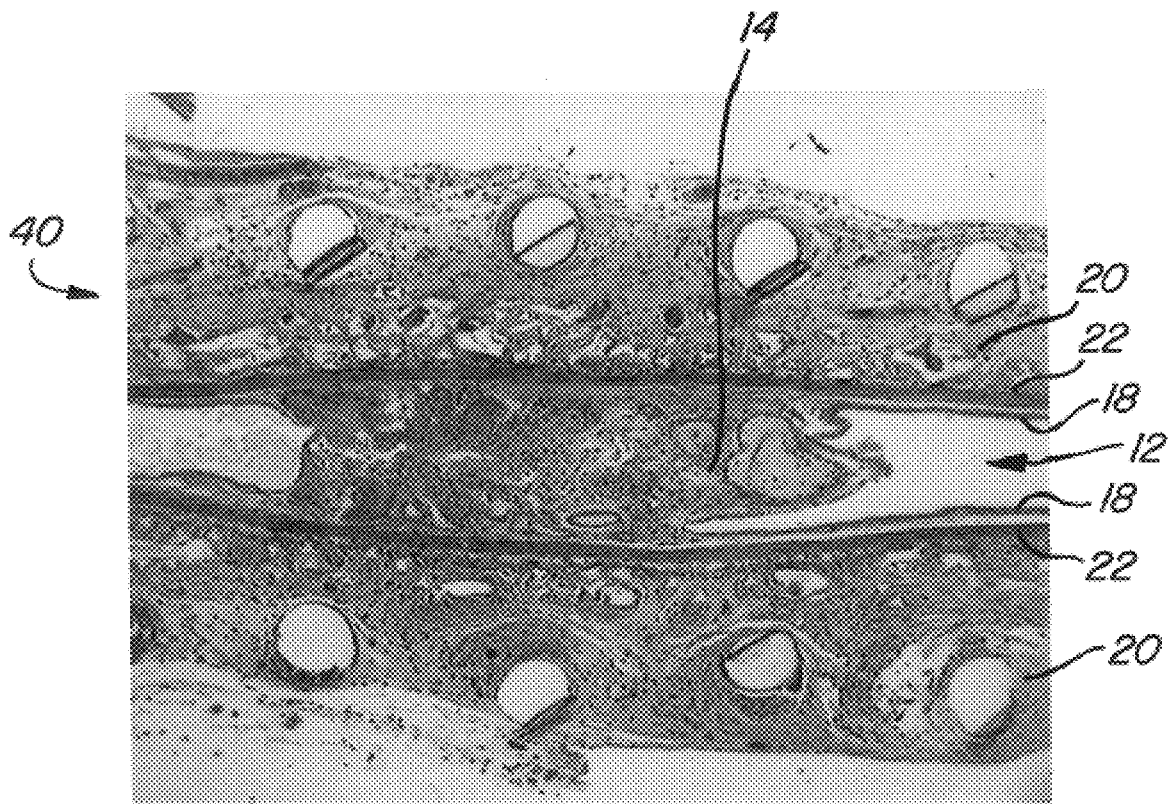
FIG. 16 is a micrograph of a formed-in-place laminated membrane structure after implantation in host rat tissue for three weeks, showing the absence of delamination.

FIG. 16 is an actual micrograph of a tri-layer cast laminate 40 made according to the invention after 3 weeks of implantation (without living lung tissue cells 14) in a rat. Like FIG. 14, FIG. 16 shows that the robust, integrated nature of the tri-layer cast laminated structure resists cellular infiltration into the formed-in-place third region, thereby preventing delamination of the overall boundary.

The demonstrated ability of third region 22 to resist delamination is not necessarily related to having an inherently high mechanical peel strength. The inventors have observed that host cells, once able to enter into a discontinuous space between the first and second regions 18 and 20, proceed to tear the first and second regions 18 and 20 apart (as FIG. 15 shows), even in the presence of a laminating material lending a high peel strength. The inventors believe that the third region 22 resists delamination because of its substantially formed-in-place, continuous configuration between the first and second regions 18 and 20 (as FIGS. 14 and 16 show). This configuration eliminates the presence of spaces and discontinuities between the first and second regions 18 and 20. As a result, the infiltration of host cells is considerably reduced. The formed-in-place, continuous configuration between the first and second regions 18 and 20 (as FIGS. 14 and 16 show). This configuration eliminates the presence of spaces and discontinuities between the first and second regions 18 and 20. As a result, the infiltration of host cells is considerably reduced. The formed-in-place laminate thus resists delamination, even should it not possess a high mechanical peel strength.

Various features of the invention are set forth in the following claims.

We claim:

1. A permeable structure forming a chamber to hold living cells, the permeable structure comprising a first permeable region surrounding at least a portion of the chamber having a conformation that, when implanted in host tissue, substantially blocks penetration of host cells into the chamber while permitting solute transport between the host and cells, a second permeable region overlying the first permeable region having a conformation that, when implanted in host tissue, forms a permeable interface with host tissue that permits solute transport between the host and cells, and a third permeable region between the first and second permeable regions comprising polymer material layer formed in place between the first and second permeable regions, the third permeable region bonding the first and second permeable regions together and having a conformation that, when implanted in host tissue, permits solute transport between the first and second permeable regions.

2. A permeable structure forming a chamber to hold living cells, the permeable structure comprising a first permeable region surrounding at least a portion of the chamber having a conformation that, when implanted in host tissue, substantially blocks penetration of host cells into the chamber while permitting solute transport between the host and cells, a second permeable region overlying the first permeable region having a conformation that, when implanted in host tissue, forms a permeable interface with host tissue that promotes the growth of vascular structures near the permeable interface while permitting solute transport between the host and cells, and a third permeable region between the first and second permeable regions comprising a polymer material layer formed in place between the first and second permeable regions, the third permeable region bonding the first and second permeable regions together and having a conformation that, when implanted in host tissue permits solute transport between the first and second permeable regions.

3. A permeable structure forming a chamber to hold living cells, the permeable structure comprising a first permeable region surrounding at least a portion of the chamber having a conformation that, when implanted in host tissue, substantially blocks penetration of host cells into the chamber while permitting solute transport between the host and cells, a second permeable region overlying the first permeable region having a conformation that, when implanted in host tissue, forms a permeable interface with host tissue that permits solute transport between the host and cells, the first permeable region comprising an array of three dimensional strands having a first dimension larger than a second and third dimensions and, for the majority of strands, neither of the second and third dimensions exceeds about 5 $\mu$m, and a third permeable region between the first and second permeable regions comprising a polymer material layer formed in place between the first and second permeable regions, the third permeable region bonding the first and second permeable regions together and having a conformation that, when implanted in host tissue, permits solute transport between the first and second permeable regions.

4. A permeable structure according to claim 1 or 2 or 3 wherein the conformation of the first permeable region, when implanted in host tissue, substantially blocks penetration of at least host tissue inflammatory cells into the chamber.

5. A permeable structure according to claim 4 wherein the conformation of the third permeable region, when implanted in host tissue, substantially blocks penetration of at least host tissue inflammatory cells into the chamber.

6. A permeable structure according to claim 1 or 2 or 3 wherein the third permeable region is in substantially continuous, intimate contact with the first and second permeable regions to substantially block infiltration of host cells between the first and second permeable regions.

7. A permeable structure according to claim 1 or 2 or 3 wherein the third permeable region penetrates at least partially into at least one of the first and second permeable regions.

8. A permeable structure according to claim 1 or 2 or 3 wherein the third permeable region has a thickness of between about 0.1 $\mu$m and 20 $\mu$m.

9. A permeable structure according to claim 1 or 2 or 3 wherein the polymer material of the third permeable region is selected from a group consisting essentially of poly (ethylene-co-vinyl alcohol), cellulose acetate, and poly (vinylidene difluoride).

10. A permeable structure according to claim 1 or 2 or 3 wherein the polymer material of the third permeable region comprises poly(ethylene-co-vinyl alcohol).

11. A permeable structure according to claim 10 wherein the polymer material of the third permeable region comprises about 3% to about 8% by weight of poly(ethylene-co-vinyl alcohol).

12. A permeable structure according to claim 1 or 2 or 3 wherein the permeable structure has a determinable first permeability value, wherein the third region has a determinable second permeability value, and wherein the second permeability is at least twice the first permeability value.

13. A permeable structure according to claim 1 or 2 or 3 and further comprising living cells in the chamber.

14. A permeable structure according to claim 13 wherein the living cells are allogeneic with respect to host tissue.

15. A permeable structure according to claim 13 wherein the living cells are isogeneic with respect to host tissue.

16. A permeable structure according to claim 1 or 2 or 3 and further comprising instructions teaching enclosure of living cells within the chamber and implantation of the permeable structure with enclosed living cells in host tissue.

17. A permeable structure forming a chamber to hold living cells, the structure comprising a permeable layer surrounding the chamber that, when implanted in host tissue, blocks contact between cells in the chamber and host cells while permitting transport of solutes between the host and cells, the permeable layer comprising a first immunoisolation region having a conformation that, when implanted in host tissue, substantially blocks penetration of host inflammatory cells, and a second immunoisolation region distinct from the first region, the second region having a conformation that, when implanted in host tissue, also substantially blocks penetration of host inflammatory cells, the first and second regions being mutually arranged in the permeable layer to together provide a redundant immunoisolation barrier.

18. A permeable structure according to claim 17 wherein the first and second immunoisolation regions contact each other in the layer.

19. A permeable structure according to claim 17 wherein the first and second immunoisolation regions are spaced apart in the layer.

20. A permeable structure according to claim 17 wherein the first immunoisolation region is formed in place in contact with the second immunoisolation region.

21. A permeable structure according to claim 17 wherein the first immunoisolation region is cast in contact with the second immunoisolation region and coagulated in place in contact with the second immunoisolation region.

22. A permeable structure forming a chamber to hold living cells, the structure comprising a permeable membrane surrounding the chamber having a conformation that, when implanted in host tissue, substantially blocks penetration of at least host inflammatory cells into the chamber while permitting solute transport between the host and cells, the permeable membrane having a surface, and an auxiliary permeable layer bonded in substantially continuous contact with the permeable membrane surface to substantially block infiltration of host cells between the auxiliary permeable layer and the permeable surface, the auxiliary permeable layer having a conformation that, when implanted in host tissue, substantially blocks penetration of at least host inflammatory cells while permitting solute transport through the permeable membrane.

23. A permeable structure forming a chamber to hold living cells, the structure comprising a permeable membrane surrounding the chamber having a conformation that, when implanted in host tissue, substantially blocks penetration of at least host inflammatory cells into the chamber while permitting solute transport between the host and cells, the permeable membrane having a surface, and an auxiliary permeable layer comprising a solution of polymer material brought into contact with the permeable membrane surface and formed in place on the permeable membrane surface, the auxiliary permeable layer having a conformation that, when implanted in host tissue, substantially blocks penetration of at least host inflammatory cells while permitting solute transport through the permeable membrane.

24. A permeable structure according to claim 23 wherein the auxiliary permeable layer is in substantially continuous, intimate contact with the permeable membrane surface to substantially block infiltration of host cells between the auxiliary permeable layer and the permeable membrane surface.

25. A permeable structure according to claim 22 or 23 wherein the auxiliary permeable layer penetrates at least partially into the permeable membrane surface.

26. A permeable structure according to claim 22 or 23 wherein the polymer material of the auxiliary permeable layer is selected from a group consisting essentially of poly(ethylene-co-vinyl alcohol), cellulose acetate, and poly (vinylidene difluoride).

27. A permeable structure according to claim 22 or 23 wherein the polymer material of the auxiliary permeable layer comprises poly(ethylene-co-vinyl alcohol).

28. A permeable structure according to claim 27 wherein the polymer material of the auxiliary permeable layer comprises about 3% to about 8% by weight of poly(ethylene-co-vinyl alcohol).

29. A permeable structure according to claim 22 or 23 and further comprising living cells in the chamber.

30. A permeable structure according to claim 29 wherein the living cells are allogeneic with respect to host tissue.

31. A permeable structure according to claim 29 wherein the living cells are isogeneic with respect to host tissue.

32. A permeable structure according to claim 22 or 23 and further comprising instructions teaching enclosure of living cells within the chamber and implantation of the permeable structure with enclosed living cells in host tissue.

* * * * *